(12) United States Patent
Schellin et al.

(10) Patent No.: US 10,251,649 B2
(45) Date of Patent: Apr. 9, 2019

(54) SURGICAL STAPLER BUTTRESS APPLICATOR WITH DATA COMMUNICATION

(71) Applicant: Ethicon Endo-Surgery, LLC, Guaynabo, PR (US)

(72) Inventors: Emily A. Schellin, Cincinnati, OH (US); Mark S. Zeiner, Mason, OH (US); Charles J Scheib, Loveland, OH (US); Prudence A. Turner, Independence, KY (US); Trevor J. Barton, Cincinnati, OH (US); Steven G. Hall, Cincinnati, OH (US); Jason L. Harris, Lebanon, OH (US); Michael J. Vendely, Lebanon, OH (US)

(73) Assignee: Ethicon LLC, Guaynabo, PR (US)

(*) Notice: Subject to any disclaimer, the term of this patent is extended or adjusted under 35 U.S.C. 154(b) by 385 days.

(21) Appl. No.: 14/926,131

(22) Filed: Oct. 29, 2015

(65) Prior Publication Data
US 2017/0119391 A1 May 4, 2017

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07292* (2013.01); *A61B 50/30* (2016.02); *A61B 90/96* (2016.02); *A61B 90/98* (2016.02); *A61B 2017/0053* (2013.01); *A61B 2017/00221* (2013.01); *A61B 2017/00734* (2013.01); *A61B 2017/00876* (2013.01); *A61B 2017/07214* (2013.01); *A61B 2090/0807* (2016.02)

(58) Field of Classification Search
CPC .......................... A61B 17/105; A61B 17/068
USPC ..... 227/176.1, 175.1, 19, 179; 606/151, 148
See application file for complete search history.

(56) References Cited

U.S. PATENT DOCUMENTS

| 4,805,823 A | 2/1989 | Rothfuss |
| 5,415,334 A | 5/1995 | Williamson et al. |

(Continued)

FOREIGN PATENT DOCUMENTS

| EP | 2 992 841 A2 | 3/2016 |
| EP | 3 135 213 A1 | 3/2017 |

OTHER PUBLICATIONS

International Search Report and Written Opinion dated Feb. 17, 2017 for Application No. PCT/US2016/057854, 14 pgs.

(Continued)

*Primary Examiner* — Nathaniel Chukwurah
(74) *Attorney, Agent, or Firm* — Frost Brown Todd LLC

(57) ABSTRACT

A buttress applier cartridge includes a housing, a platform, a buttress assembly, and a data communication feature. The housing defines a gap that is configured to receive a portion of an end effector of a surgical stapler. A portion of the platform is exposed in the gap defined by the housing. The buttress assembly is positioned on the platform. The buttress assembly is exposed in the gap defined by the housing. The data communication feature is configured to provide communication of data relating to the cartridge. The data communication feature may communicate with a complementary data communication feature of the surgical stapler.

19 Claims, 15 Drawing Sheets

(51) Int. Cl.
*A61B 17/068* (2006.01)
*A61B 50/30* (2016.01)
*A61B 17/00* (2006.01)
*A61B 90/96* (2016.01)
*A61B 90/98* (2016.01)
*A61B 90/00* (2016.01)

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,752,965 A * | 5/1998 | Francis ............ A61B 17/07207 227/178.1 |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,939,358 B2 * | 9/2005 | Palacios ............ A61B 17/07207 606/151 |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney |
| 7,691,098 B2 | 4/2010 | Wallace |
| 7,721,930 B2 | 5/2010 | McKenna et al. |
| 7,806,891 B2 | 10/2010 | Nowlin et al. |
| 8,044,778 B2 | 10/2011 | Monroe |
| 8,141,762 B2 | 3/2012 | Bedi et al. |
| 8,210,411 B2 | 7/2012 | Yates et al. |
| 8,371,491 B2 | 2/2013 | Huitema et al. |
| 8,408,439 B2 | 4/2013 | Huang et al. |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,899,464 B2 | 12/2014 | Hueil et al. |
| 8,998,060 B2 | 4/2015 | Bruewer et al. |
| 9,101,359 B2 | 8/2015 | Smith et al. |
| 9,186,142 B2 | 11/2015 | Fanelli et al. |
| 9,198,644 B2 | 12/2015 | Balek et al. |
| 9,211,120 B2 | 12/2015 | Scheib et al. |
| 9,301,759 B2 | 4/2016 | Spivey et al. |
| 9,393,018 B2 | 7/2016 | Wang et al. |
| 9,398,911 B2 | 7/2016 | Auld |
| 9,492,170 B2 | 11/2016 | Bear et al. |
| 9,517,065 B2 | 12/2016 | Simms et al. |
| 9,649,113 B2 | 5/2017 | Ma et al. |
| 2005/0070929 A1 * | 3/2005 | Dalessandro .... A61B 17/07207 606/151 |
| 2005/0131390 A1 * | 6/2005 | Heinrich ............ A61B 17/0469 606/1 |
| 2008/0169328 A1 | 7/2008 | Shelton, IV |
| 2009/0206142 A1 * | 8/2009 | Huitema .......... A61B 17/07207 227/176.1 |
| 2012/0241493 A1 | 9/2012 | Baxter, III et al. |
| 2012/0289979 A1 * | 11/2012 | Eskaros ........... A61B 17/07292 606/151 |
| 2013/0062391 A1 | 3/2013 | Boudreaux et al. |
| 2013/0068816 A1 | 3/2013 | Vasudevan et al. |
| 2013/0075447 A1 | 3/2013 | Weisenburgh, II et al. |
| 2013/0206813 A1 | 8/2013 | Nalagatla |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0263563 A1 | 9/2014 | Stokes et al. |
| 2015/0272575 A1 | 10/2015 | Leimbach et al. |
| 2015/0351754 A1 | 12/2015 | Harris et al. |
| 2015/0351758 A1 | 12/2015 | Shelton, IV et al. |
| 2015/0351763 A1 | 12/2015 | Shelton, IV et al. |
| 2015/0374360 A1 | 12/2015 | Scheib et al. |
| 2015/0374373 A1 | 12/2015 | Rector et al. |
| 2016/0089146 A1 | 3/2016 | Harris et al. |
| 2016/0278774 A1 | 9/2016 | Shelton, IV et al. |

OTHER PUBLICATIONS

European Search Report and Written Opinion dated Feb. 16, 2017 for Application No. EP 16196245.1, 8 pgs.
U.S. Appl. No. 62/209,041, filed Aug. 24, 2015.
U.S. Appl. No. 14/827,856, filed Aug. 17, 2015.
U.S. Appl. No. 14/840,613, filed Aug. 31, 2015.
U.S. Appl. No. 14/871,071, filed Sep. 30, 2015.
U.S. Appl. No. 14/871,131, filed Sep. 30, 2015.
European Examination Report dated Feb. 28, 2018 for Application No. EP 16196245.1, 4 pgs.

* cited by examiner

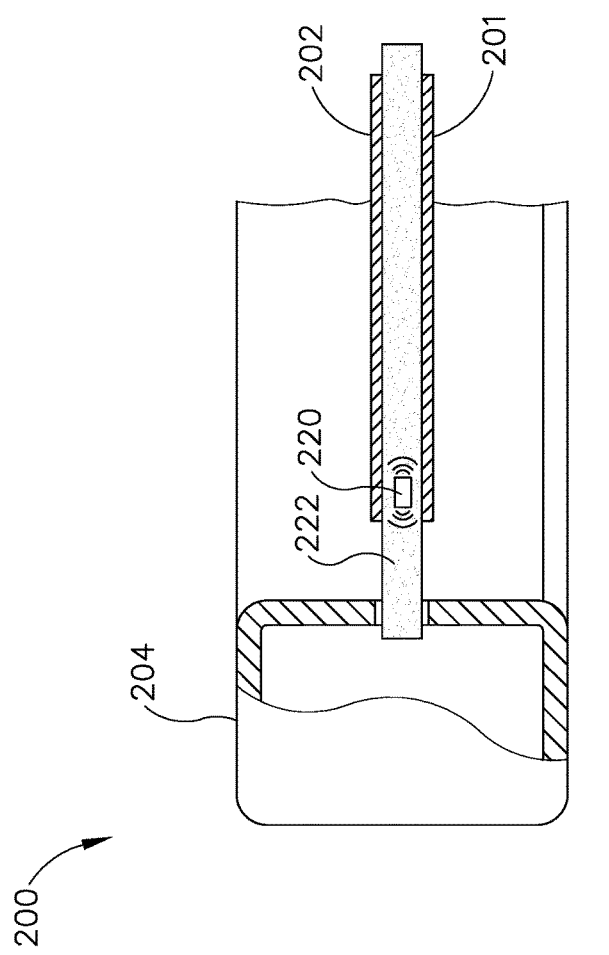

SURGICAL STAPLER BUTTRESS APPLICATOR WITH DATA COMMUNICATION

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, issued as U.S. Pat. No. 9,936,954 on Apr. 10, 2018, entitled "Devices and Methods for Sealing Staples in Tissue"; and U.S. patent application Ser. No. 14/498,070, entitled "Radically Expandable Staple Line" filed Sep. 26, 2014, published as U.S. Pub. No. 2016/0089146 on Mar. 31, 2016. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 13A depicts a cross-sectional side view of the buttress applier cartridge of FIG. 7, loaded with upper and lower buttress assemblies;

Figure 1:
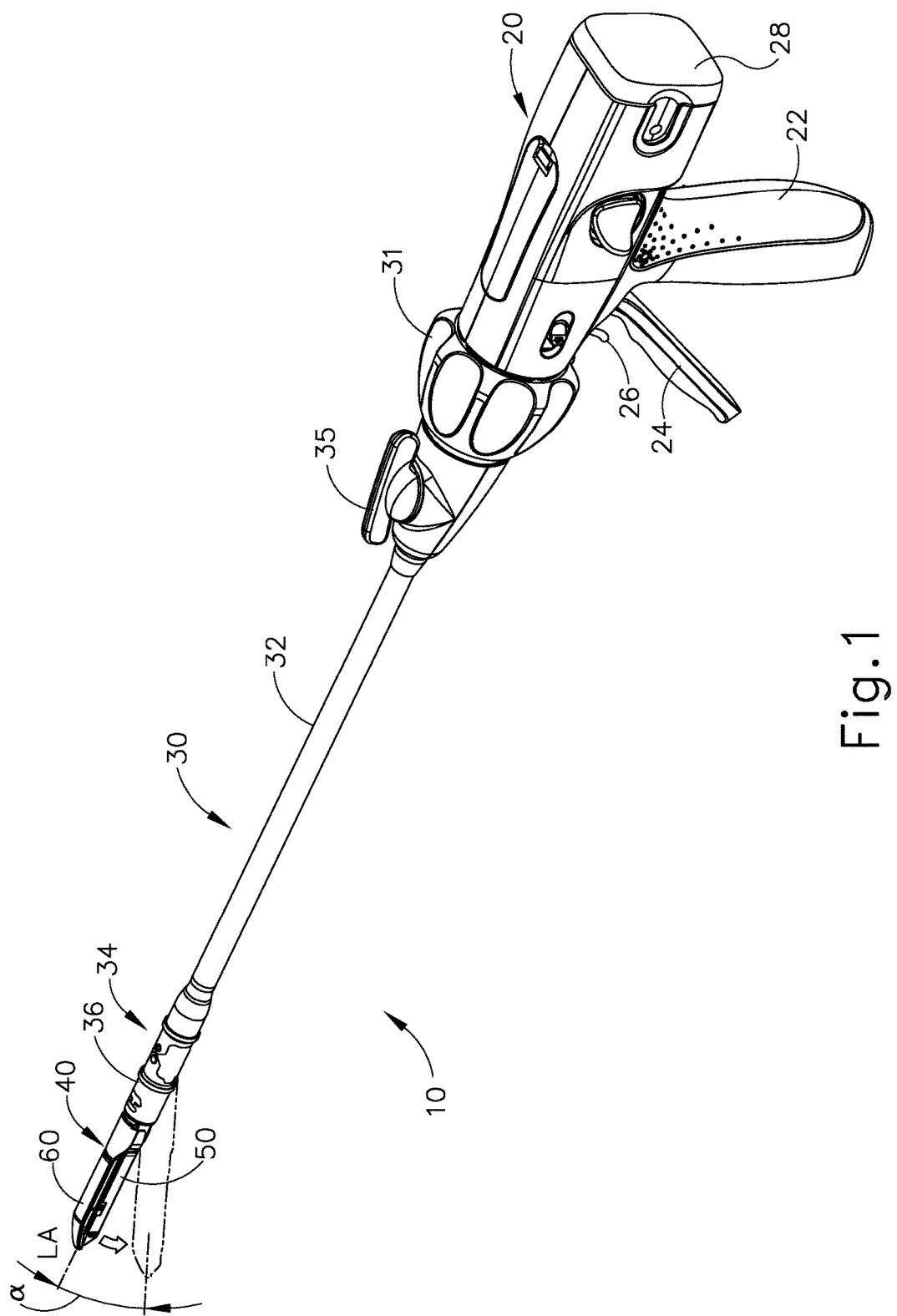
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
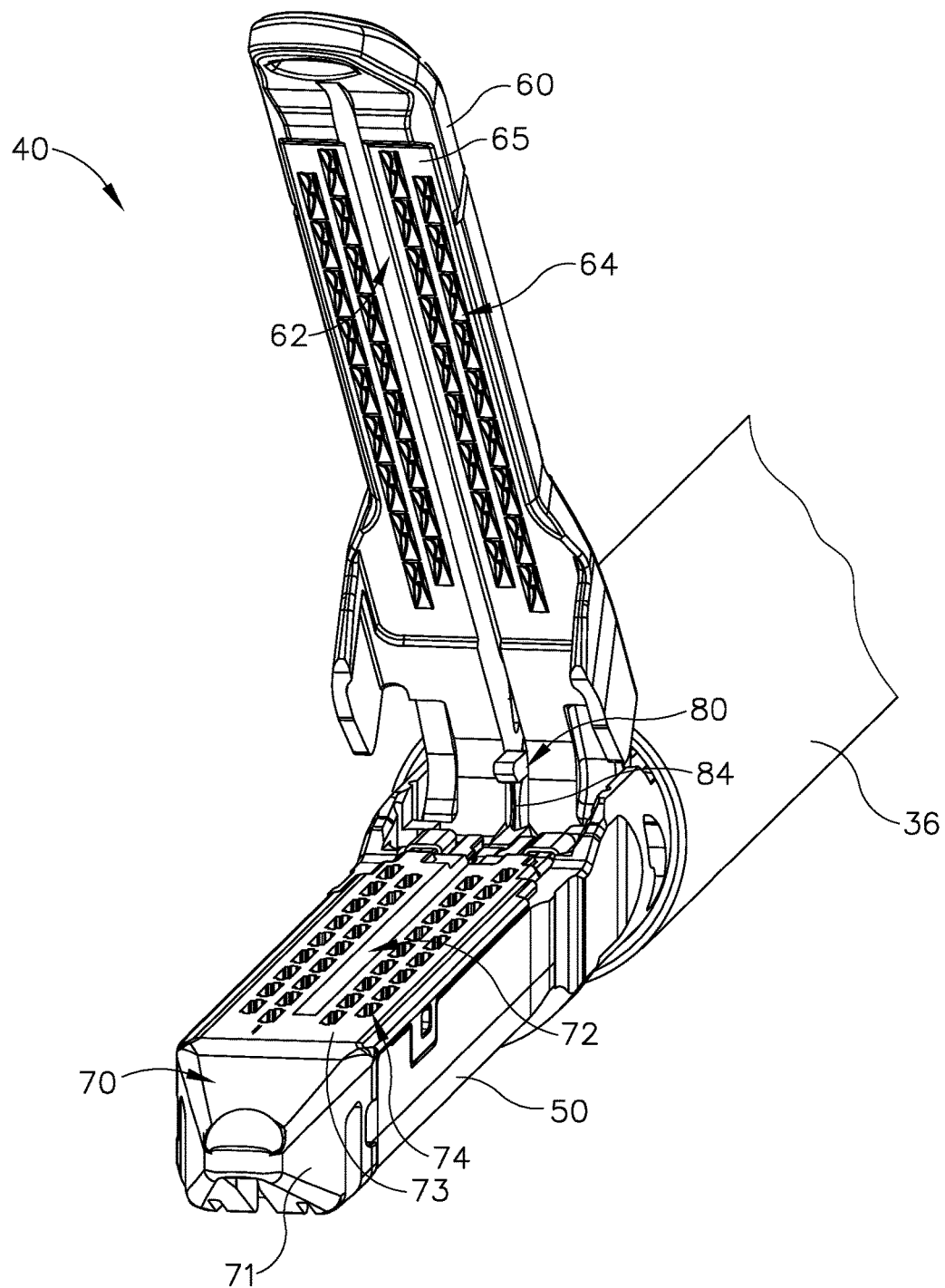
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. patent application Ser. No. 14/314,125, entitled "Articulation Drive Features for Surgical Stapler," filed Jun. 25, 2014, published as U.S. Pub. No. 2015/0374360 on Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
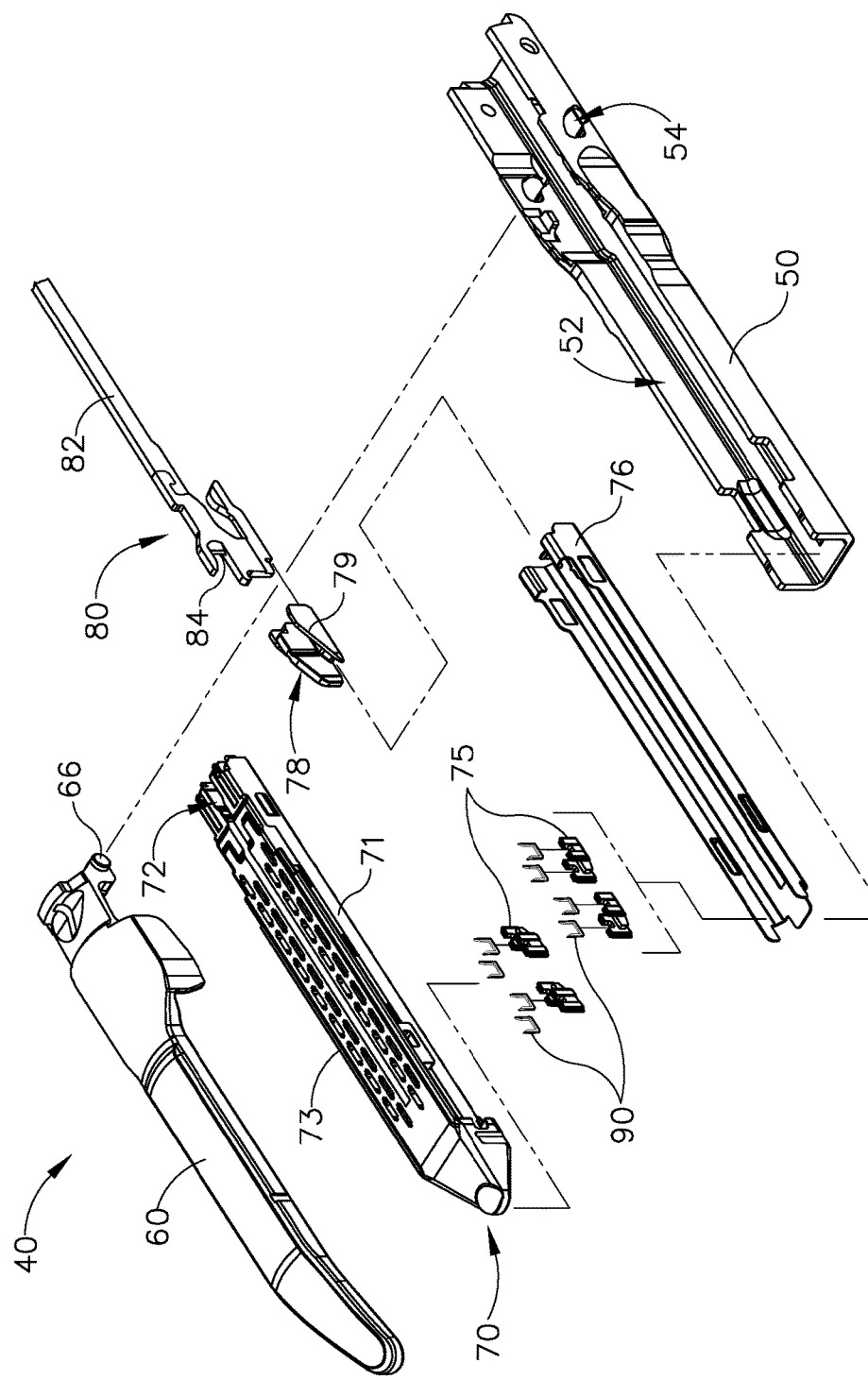
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373 on Dec. 31, 2015, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
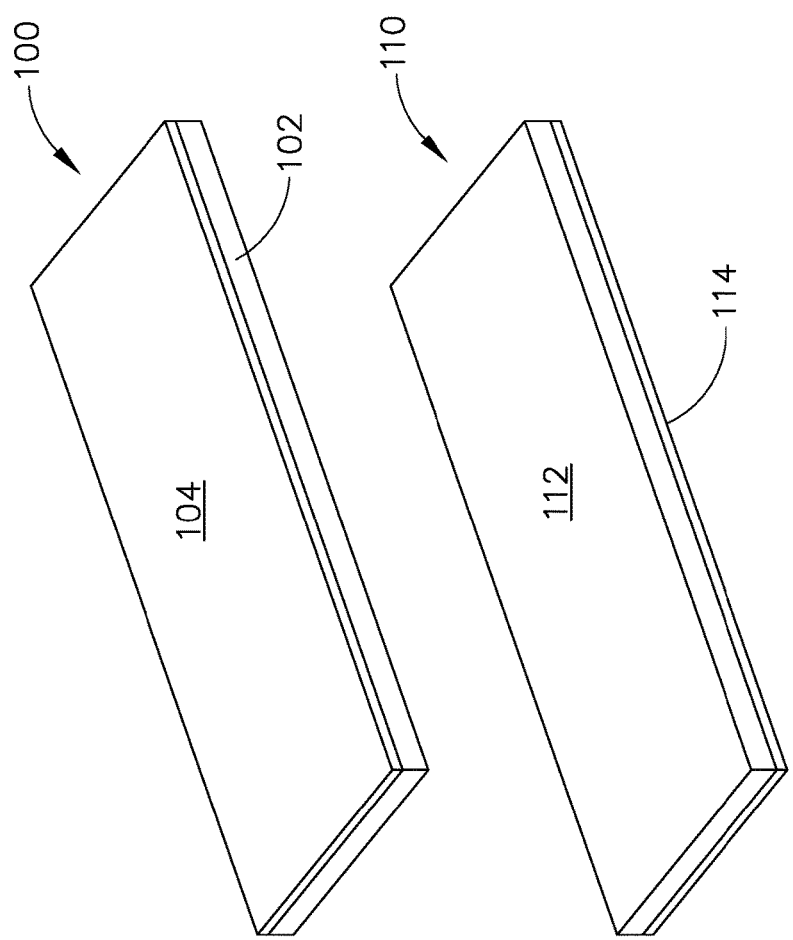
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, published as U.S. Pat. No. 2016/0278774 on Sep. 29, 2016, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,789 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No.

2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Pub. No. 2017/0055986 on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and/or U.S. patent application Ser. No. 14/871,131, entitled "Method for Applying an Implantable Layer to a Fastener Cartridge," field Sep. 30, 2015, published as U.S. Pub. No. 2017/0086842 on Mar. 30, 2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5:
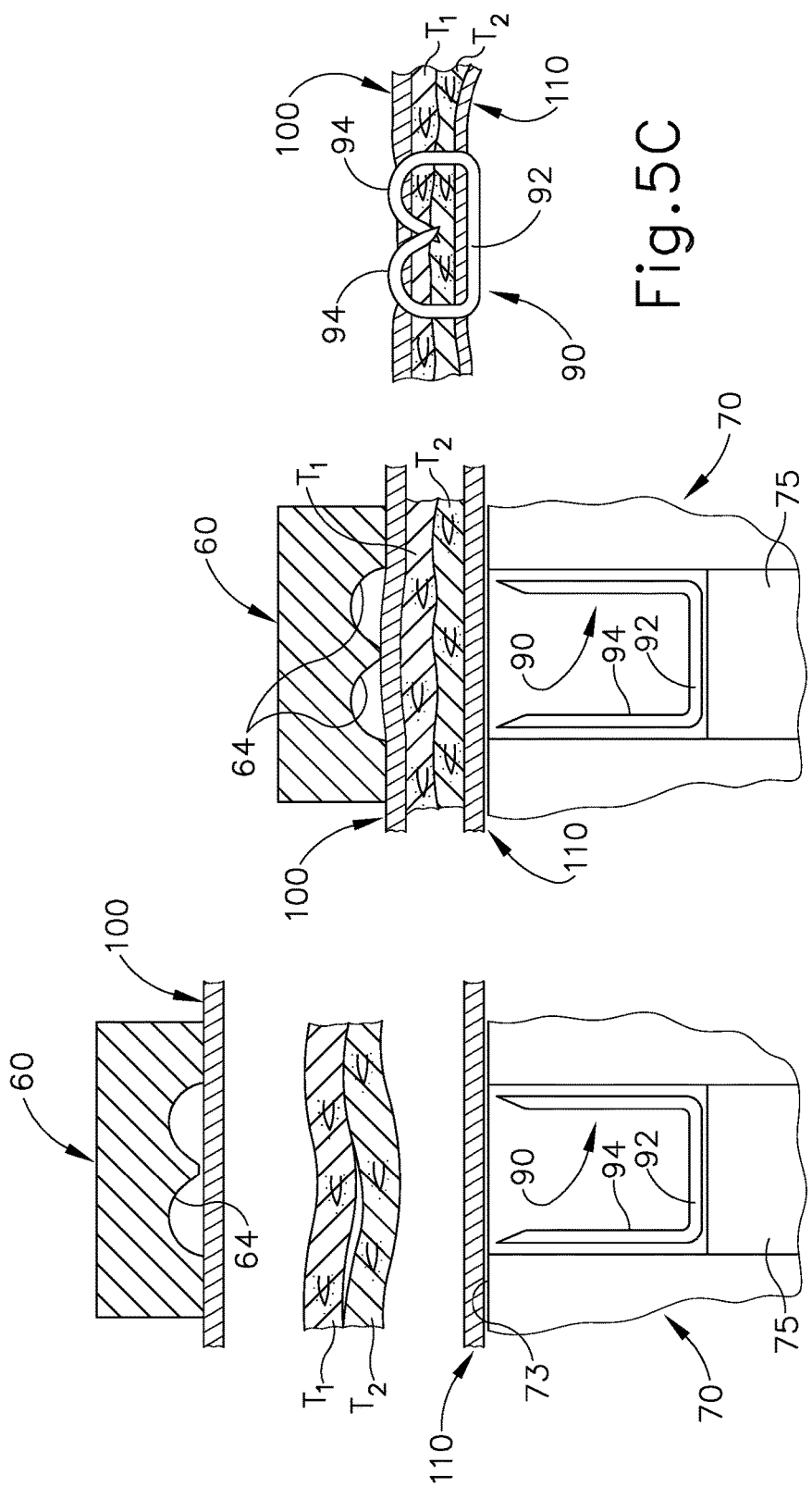
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
FIG. 5B depicts a cross-sectional end view of the combined end effector and buttress assembly of FIG. 5A, with tissue positioned between the buttresses in the end effector, and with the anvil in a closed position.
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
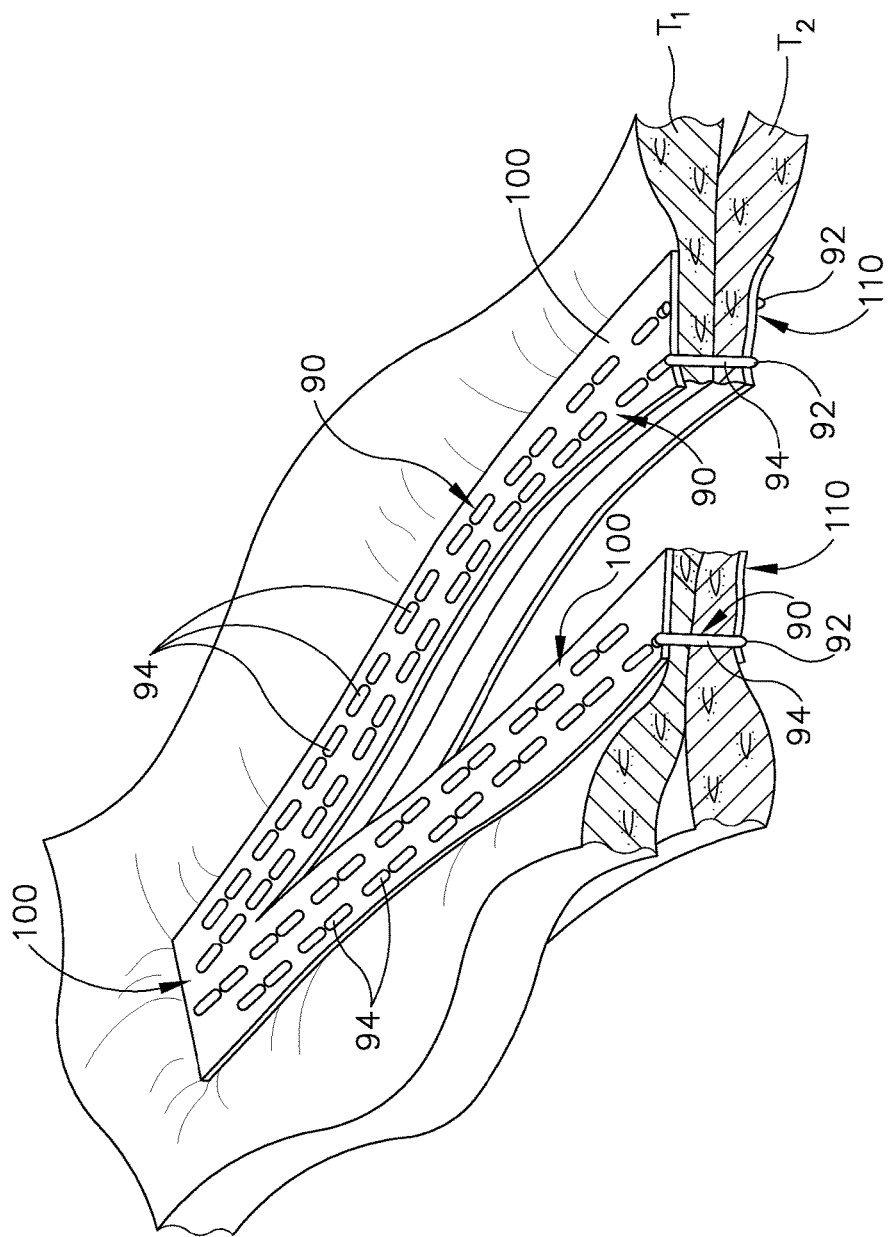
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

III. Exemplary Buttress Applier Cartridge with Data Communication

As noted above, buttress assembly (100) may be applied to the underside (65) of anvil (60), and buttress (110) may be applied to deck (73) of staple cartridge (70), before tissue ($T_1$, $T_2$) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to cartridge assemblies that provide such support, protection, and loading of buttress assemblies (100, 110). It should be understood that the following examples are merely illustrative. Numerous variations will be apparent to those of ordinary skill in the art in view of the teachings herein.

Figure 7:
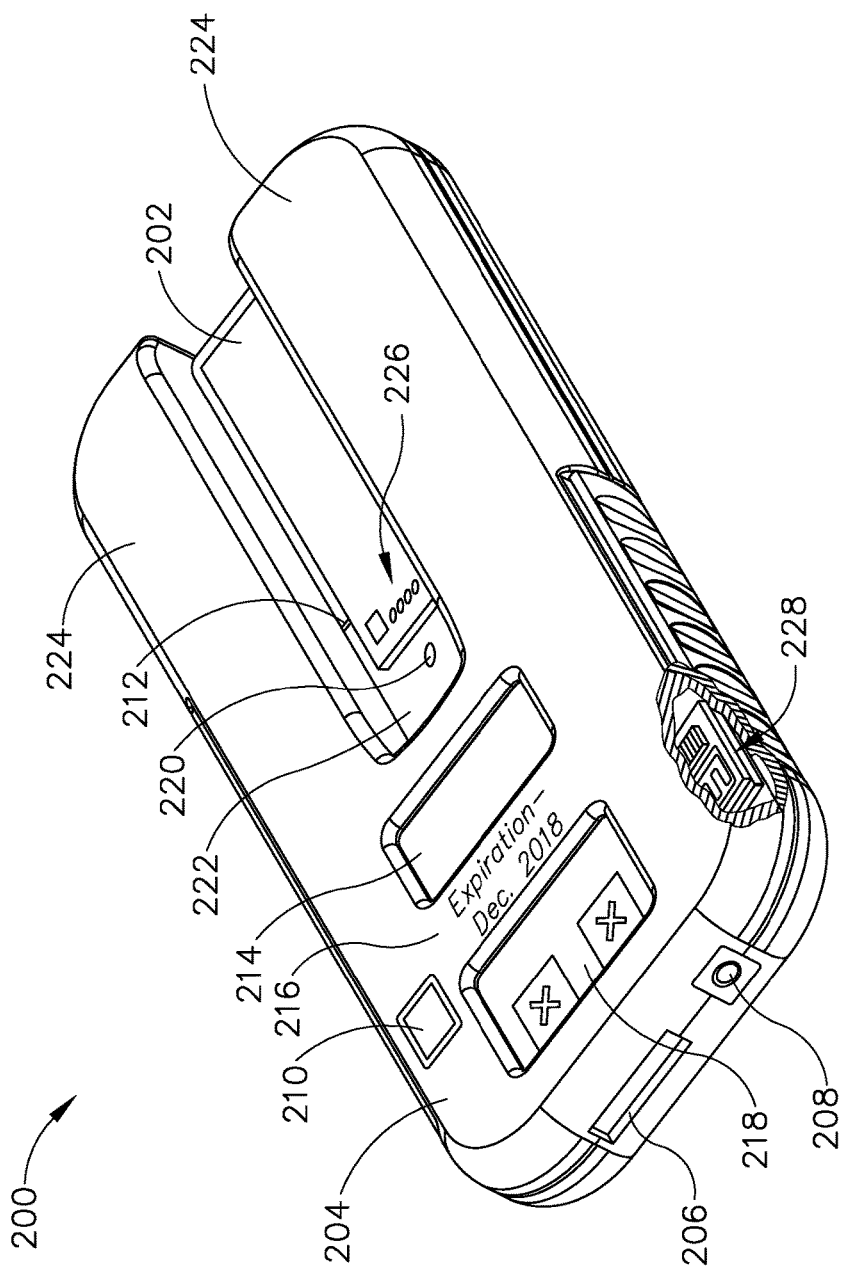
FIG. 7 depicts a perspective view of an exemplary buttress applier cartridge that may be used to carry and apply the buttress assembly of FIG. 5A.
Figure 8:
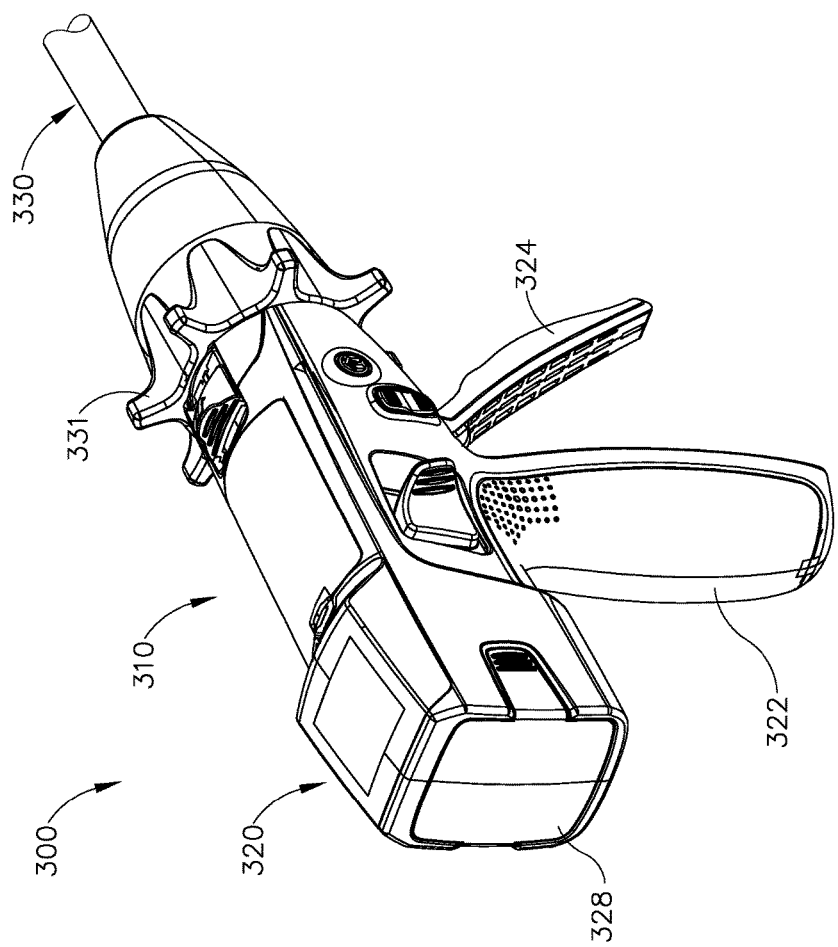
FIG. 8 depicts a perspective view of a handle assembly of an exemplary alternative surgical stapling instrument.

FIG. 7 shows an exemplary buttress applier cartridge (200) that may be used in conjunction with an exemplary alternative surgical stapling and severing instrument (300) as shown in FIG. 8. Cartridge (200) of this example comprises a "U" shaped housing (204) that defines two prongs (224) having a space therebetween. As described in greater detail below, this space is sized to accommodate the length and width of an end effector (340) of instrument (300). A platform (222) is located in the space between prongs (224). A buttress (202) is supported on platform (222).

Figure 13B:
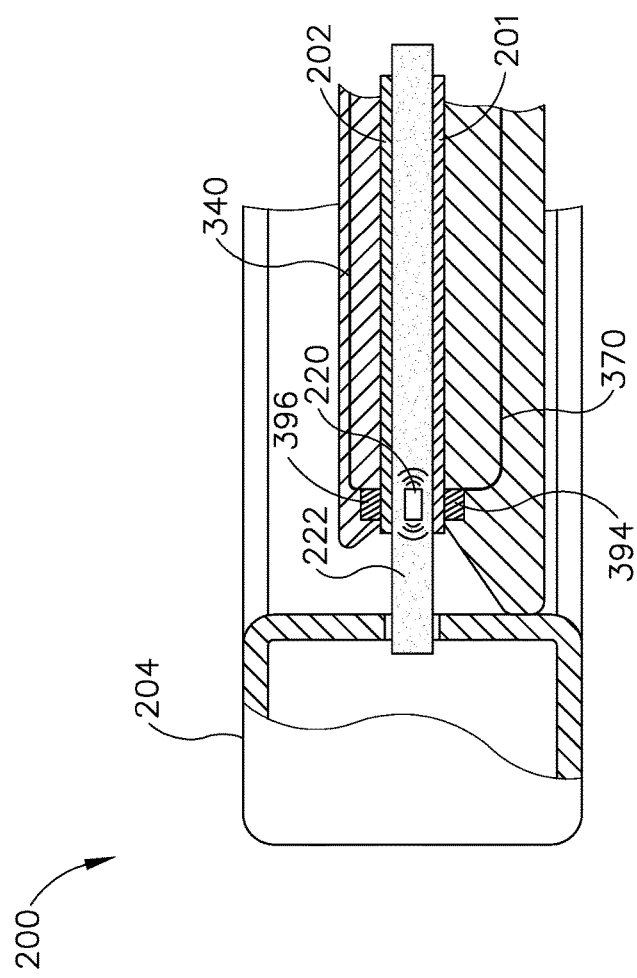
FIG. 13B depicts a cross-sectional side view of the buttress applier cartridge of FIG. 7, with the end effector of FIG. 9 clamped down on the buttress assemblies.

By way of example only, platform (222) may comprise a sheet of foam material. While only one buttress (202) is shown on the top side of platform (222) in FIG. 7, it should be understood that another buttress (201) may be positioned on the underside of platform (222), as shown in FIGS. 13A-13B. Buttresses (201, 202) may be removably secured to platform (222) in any suitable fashion, including but not limited to being secured via an adhesive, resiliently biased retainers, etc. As another merely illustrative example, buttresses (201, 202) may be removably secured to platform (222) in accordance with at least some of the teachings of U.S. Patent App. No. 62/209,041, entitled "Method and Apparatus for Applying a Buttress to End Effector of a Surgical Stapler," filed Aug. 24, 2015, the disclosure of which is incorporated by reference herein. Other suitable ways in which buttresses (201, 202) may be removably secured to platform (222) will be apparent to those of ordinary skill in the art in view of the teachings herein.

While cartridge (200) may be used with instrument (10) described above, cartridge (200) is particularly configured to be used with instrument (300). Instrument (300) of this example is configured and operable just like instrument (10) except for the differences described below. It should also be understood that instrument (300) may be configured and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein. As shown in FIG. 8, instrument (300) of this example comprises a handle assembly (310) with a display screen (320), a pistol grip (322), a pivoting trigger (324), and a removable battery pack (328). A shaft assembly (330) extends distally from handle assembly (310). A rotary knob (331) is located at the proximal end of shaft assembly (330) and is operable to rotate shaft assembly (330) relative to handle assembly (310), about the longitudinal axis of shaft assembly (330). Shaft assembly (330) of this example is substantially identical to shaft assembly (30) described above, except that shaft assembly (330) of this example includes one or more wires and/or other features that enable communication of data from end effector (40) to handle assembly (310). In some versions, shaft assembly (330) is selectively removable from handle assembly (310) (e.g., in accordance with the teachings of U.S. patent application Ser. No. 14/226,142, issued as U.S. Pat. No. 9,913,642 on Mar. 13, 2018, or in any other suitable fashion).

Figure 9:
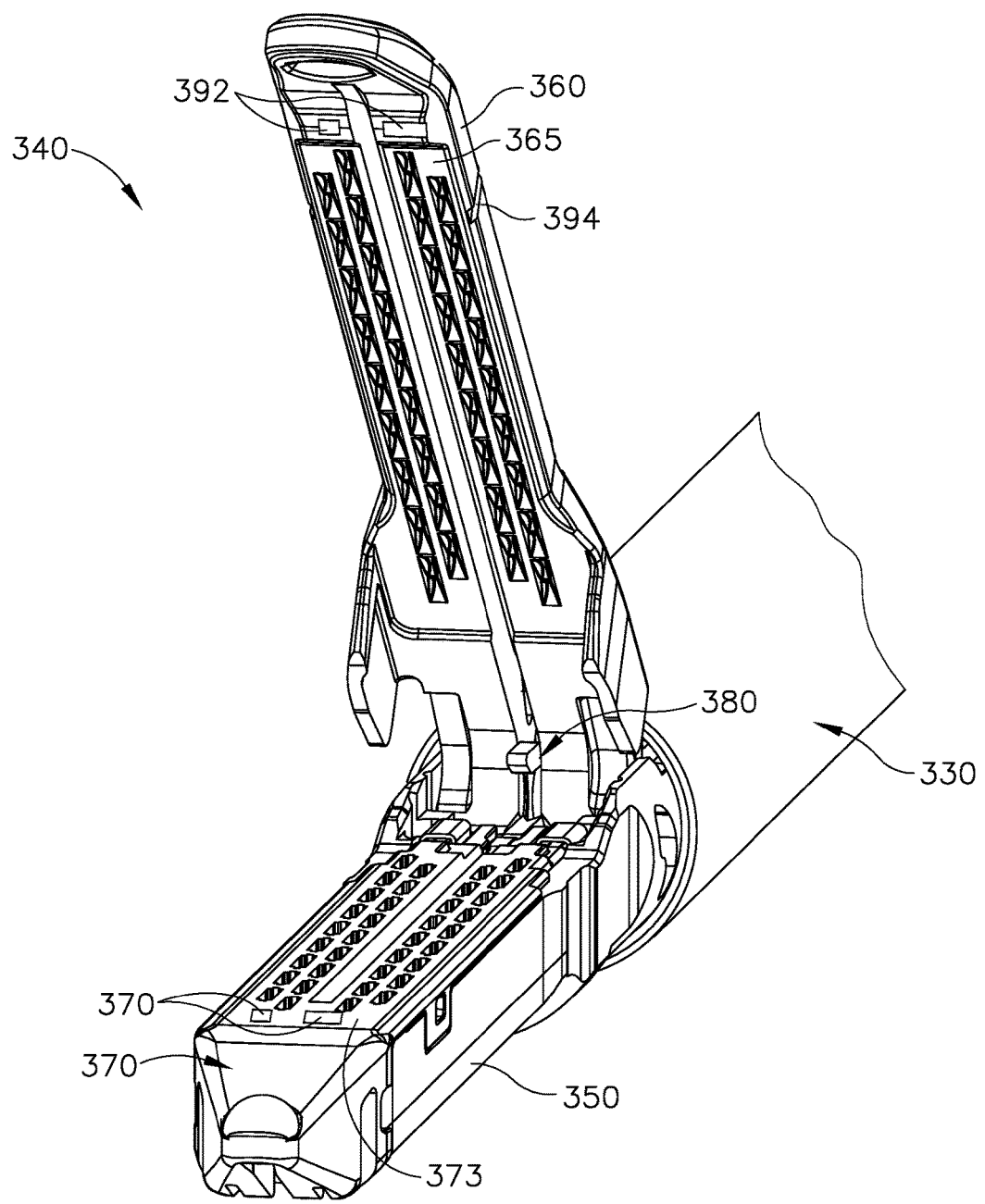
FIG. 9 depicts a perspective view of an end effector of the instrument of FIG. 8, with the end effector in an open configuration.
Figure 10:
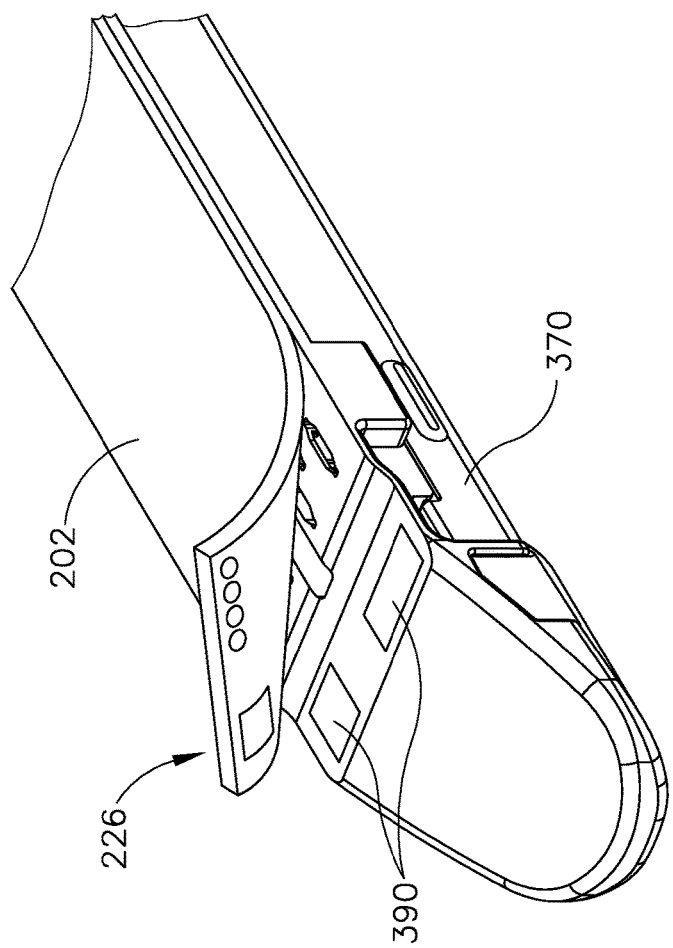
FIG. 10 depicts a partial perspective view of the distal end of a staple cartridge of the end effector of FIG. 9, with a buttress assembly of the buttress applier cartridge of FIG. 7 engaging a deck of the staple cartridge.

As shown in FIG. 9, an end effector (340) is positioned at the distal end of shaft assembly (330). End effector (330) includes a lower jaw (350), an anvil (360), and a staple cartridge (370) that is removably received in lower jaw (350). A knife member (380) is configured to translate through end effector (340) to sever tissue that is captured between underside (365) of anvil (360) and deck (373) of staple cartridge (370). Knife member (380) also cooperates with a wedge sled (not shown) in staple cartridge (370) to drive staples from staple cartridge (370), through the captured tissue, and into formation against anvil (360). In the present example, pivotal movement of trigger (324) toward and away from pistol grip (322) will pivot anvil (360) toward and away from staple cartridge (373). In addition, pivoting of a firing trigger (not shown) on handle assembly (310) will drive knife member (380) distally through end effector (340). It should therefore be understood that end effector (340) and handle assembly (310) are configured and operable substantially similar to end effector (40) and handle assembly (20) described above. However, unlike end effector (40), end effector (340) of this example comprises a set of sensors (390, 392, 394, 396) and a marking (394). These features will be described in greater detail below.

While end effector (340) is described in the present example as being coupled with handle assembly (310) of FIG. 8, it should be understood that the present teachings may also be readily applied in versions where end effector (340) is incorporated into a robotic surgical system. For instance, end effector (340) may be readily incorporated into any of the various robotic surgical systems that are described in the references cited below; and cartridge (200) may also be readily used in such a combination. Other suitable ways in which end effector (340) may be incorporated into various kinds of robotic surgical systems, as well as various ways in which cartridge (200) may be used in such systems, will be apparent to those of ordinary skill in the art in view of the teachings herein.

Referring back to FIG. 7, cartridge (200) of the present example further includes an internal battery (not shown), a data port (206), a battery recharge port (208), a data transmitter (210), a status indicator window (214), an expiration date listing (216), an environmental condition indicator (218), and an integral circuit board (228). Circuit board (228) includes (or is at least in communication with) all of the electronic circuit components that provide the operability described herein. Various suitable components and arrangements that may be incorporated into circuit board (228) will be apparent to those of ordinary skill in the art in view of the teachings herein. Circuit board (228) is powered by the internal battery. By way of example only, the internal battery may comprise a button cell battery and/or any other suitable kind of battery. In the present example, the battery is rechargeable, though it should be understood that other versions may include non-rechargeable batteries.

Data port (206) is configured to enable wired communication between one or more components that are on or otherwise coupled with circuit board (228) and an external computing device (e.g., desktop computer, laptop computer, tablet computer, smartphone, robotic surgical system, etc.). Data port (206) may thus be used to communicate data from cartridge (200) to the external device. For instance, data port (206) may be used to communicate any of the various kinds of information identified as being communicated below with respect to communication between cartridge (200) and instrument (300). In addition or in the alternative, data port (206) may be used to communicate data from the external device to cartridge (200). For instance, data port (206) may be used to provide firmware updates, new information about buttresses (201, 202), and/or other information to cartridge (200).

Battery recharge port (208) is operable to couple with a wire to provide electrical power that recharges the internal battery in cartridge (200). In some variations, battery recharge port (208) comprises an inductive coil that is configured to provide wireless electrical recharging of the internal battery in cartridge (200). Various suitable ways in which the internal battery in cartridge (200) may be recharged will be apparent to those of ordinary skill in the art in view of the teachings herein. It should also be understood that some versions may lack recharging capability, such that the internal battery in cartridge (200) is non-rechargeable. Still other versions of cartridge (200) may lack an internal battery altogether. For instance, cartridge (200) may include one or more photovoltaic cells that are configured to provide electrical power. As yet another merely illustrative variation, cartridge (200) may lack electrically powered components altogether.

Data transmitter (210) is configured to provide wireless communication between cartridge (200) and instrument (300) and/or other external devices (e.g., desktop computer, laptop computer, tablet computer, smartphone, robotic surgical system, etc.). While not shown, it should be understood that instrument (300) may include a data transmitter that is configured to communicate wirelessly with data transmitter (210) of cartridge (200). By way of example only, data transmitter (210) may be configured to communicate wirelessly using the Bluetooth protocol, the Zigbee protocol, and/or any other suitable wireless communication protocol as will be apparent to those of ordinary skill in the art in view of the teachings herein. In some instances, data transmitter (210) only transmits data one way, to instrument (300) and/or other external devices. In some other instances, data transmitter (210) only receives data one way, from instrument (300) and/or other external devices. Alternatively, data transmitter (210) may provide bi-directional communication with instrument (300) and/or other external devices. Various suitable forms that transmitter (210) may take will be apparent to those of ordinary skill in the art in view of the teachings herein.

By way of example only, the data communicated by transmitter (210) may include information relating to the kinds of buttresses (201, 202) on platform (222), information relating to the lot number and/or expiration date associated with buttresses (201, 202) on platform, information relating to environmental conditions (e.g., temperature, humidity, etc.) that have been encountered by cartridge (200), and/or any other suitable kind of information as will be apparent to those of ordinary skill in the art in view of the teachings herein. In some versions, cartridge (200) is continuously powered by its internal battery and continuously tracks data associated with environmental conditions (e.g., temperature, humidity, etc.) that have been encountered by cartridge (200), then automatically transmits the information to instrument (300) via transmitter (210) in response to end effector (340) coming into sufficient proximity to cartridge (200). It should therefore be understood that cartridge (200) and end effector (340) may include complementary features that enable cartridge (200) to determine when end effector (340) has come within sufficient proximity to cartridge (200). Various suitable forms that such features may take will be apparent to those of ordinary skill in the art in view of the teachings herein. In some versions, transmitter (210) sends the information to instrument (300) In response to end effector (340) being clamped on buttresses (201, 202) and platform (222); and/or when end effector (340) pulls buttresses (201, 202) away from platform (222).

Status indicator window (214) of the present example is configured to indicate status information relating to cartridge (200) and/or buttresses (201, 202). In some versions, status indicator window (214) provides a fixed display, such as information printed on a sticker or card, etc. In some other versions, status indicator window (214) provides a dynamic display, such as information rendered through an LCD screen, LED screen, and/or other form of display. By way of example only, status indicator window (214) may indicate the kind of buttresses (201, 202) that are positioned on platform (222), such as by reference to a type number or some other representation. The operator may view this type number and thereby understand what kind of buttresses (201, 202) are positioned on platform (222) (e.g., whether they have a certain kind of medicament, what material(s) they are formed of, what kinds of surgical procedures they are intended for, etc.). While similar information may be rendered through display screen (320) based on a reading of indicia (226) by sensors (390, 392), having such information through status indicator window (214) may enable the operator to select an appropriate cartridge (200) when presented with various cartridges (200) to choose from. Moreover, the operator may confirm that the information presented through display screen (320) is consistent with the information presented through status indicator window (214). Other suitable information about buttresses (201, 202) that may be presented through status indicator window (214) will be apparent to those of ordinary skill in the art in view of the teachings herein.

In addition to or as an alternative to presenting information about buttresses (201, 202), status indicator window (214) may present information about the state of cartridge (200). For instance, status indicator window (214) may indicate whether cartridge (200) is ready for use. It should also be understood that environmental condition indicator (218) may be readily integrated into status indicator window (214). Environmental condition indicator (218) will be described in greater detail below. Other suitable kinds of information that may be provided through status indicator window (214) will be apparent to those of ordinary skill in the art in view of the teachings herein.

It should be understood that some versions of buttresses (201, 202) may include one or more materials whose effectiveness, integrity, and/or other characteristics may degrade over a period of time. It may therefore be desirable to indicate to the operator when that time has been reached (or when a time has been reached that is some predetermined duration before the degradation of buttress (201, 202) would be expected). To that end, expiration date listing (216) simply lists an expiration date for buttresses (201, 202), directly on housing (204) of cartridge (200) to enable ready visibility. It should be understood that the operator may alternatively be informed of an expiration date in any other suitable fashion, such that cartridge (200) may lack expiration date listing (216) in some versions.

Some versions of buttresses (201, 202) may include materials that are sensitive to environmental conditions, including but not limited to temperature and/or humidity. For instance, buttresses (201, 202) may transition to an undesirable state if buttresses (201, 202) encounter a temperature that is either above or below thresholds that provide upper and lower bounds, respectively, of a predetermined range. Likewise, buttresses (201, 202) may transition to an undesirable state if buttresses (201, 202) encounter a humidity level that is either above or below thresholds that provide upper and lower bounds, respectively, of a predetermined range. To that end, environmental condition indicator (218) is configured to indicate environmental conditions encountered by cartridge (200). In some versions, environmental condition indicator (218) is printed with environmentally sensitive ink whose properties change in response to environmental conditions. For instance, environmental condition indicator (218) may be configured to present a checkmark when the humidity level is within an appropriate range; and present an "X" when the humidity level is outside the appropriate range. Similarly, environmental condition indicator (218) may be configured to present a checkmark when the temperature level is within an appropriate range; and present an "X" when the temperature level is outside the appropriate range. It should also be understood that environmental condition indicator (218) may include two or more regions. For instance, environmental condition indicator (218) may have one region that is responsive to humidity, one region that is responsive to temperature, etc. Other suitable conditions that environmental condition indicator (218) may respond to will be apparent to those of ordinary skill in the art in view of the teachings herein.

Moreover, various suitable inks, features, and/or other components that may be used to form environmental condition indicator (218) will be apparent to those of ordinary skill in the art in view of the teachings herein. While environmental condition indicator (218) of the above-described example is passive, some versions of environmental condition indicator (218) may be active (i.e., electrically powered). It should also be understood that environmental condition indicator (218) may simply indicate present environmental conditions in real time. In some versions, however, environmental condition indicator (218) is configured to maintain an indication that one or more environmental conditions has fallen outside of an acceptable range, even if such environmental conditions return to the acceptable range. For instance, if cartridge (200) is exposed to an unacceptably high temperature or humidity level, the state of environmental condition indicator (218) may change to indicate that such level has exceeded an appropriate threshold; and environmental condition indicator (218) may maintain that changed state even after the temperature or humidity level falls back below the threshold. Various suitable ways in which environmental condition indicator (218) may maintain a changed state despite a return in environmental conditions will be apparent to those of ordinary skill in the art in view of the teachings herein.

Buttresses (201, 202) of the present example are substantially identical to buttress assemblies (100, 110) described above, except that buttresses (201, 202) of the present example comprises indicia (226) that are configured to be read by sensors (390, 392) (FIG. 9) on end effector (360). In the present example, indicia (226) are printed on buttresses (201, 202), though it should be understood that indicia (226) may alternatively be otherwise applied to or otherwise integrated into buttresses (201, 202). Indicia (226) are configured to indicate the type of buttresses (201, 202), such as whether buttresses (201, 202) carry certain kinds of medicaments, such as whether buttresses (201, 202) have certain structural properties, the length of buttresses (201, 202), etc. Indicia (226) may also convey information such as the lot number, expiration date, and/or other data associated with buttresses (201, 202). Other suitable ways in which buttresses (201, 202) may vary, and how such variations may be conveyed through indicia (226), will be apparent to those of ordinary skill in the art in view of the teachings herein.

In the present example, sensors (390, 392) comprise optical sensors and indicia (226) comprise QR codes or some other form of optical coding, such that sensors (390, 392) are operable to read indicia (226) by viewing indicia (226). In some other versions, sensors (390, 392) comprise RFID readers and indicia (226) comprise RFID chips, such that sensors (390, 392) read indicia (226) through RFID sensing. Other suitable forms that sensors (390, 392) and indicia (226) can take will be apparent to those of ordinary skill in the art in view of the teachings herein. Regardless of the form of indicia (226) and sensors (390, 392), instrument (300) may process the data from indicia (226) in various ways. For instance, if instrument (300) determines that the operator is attempting to load end effector (340) with buttresses (201, 202) that are not configured for use with that particular end effector (340), a control logic in instrument (300) may notify the operator (e.g., via display screen (320)) and, in some versions, prevent usage of instrument (300). In addition or in the alternative, instrument (300) may vary the force and/or speed with which knife member (380) is driven based on the detected kind of buttresses (201, 202) loaded on end effector (340). In addition or in the alternative, instrument (300) may vary the closure force or closure gap provided through end effector (340) based on the detected kind of buttresses (201, 202) loaded on end effector (340). Other various ways in which instrument (300) may respond based on the detected kind of buttresses (201, 202) loaded on end effector (340) will be apparent to those of ordinary skill in the art in view of the teachings herein.

Figure 11:
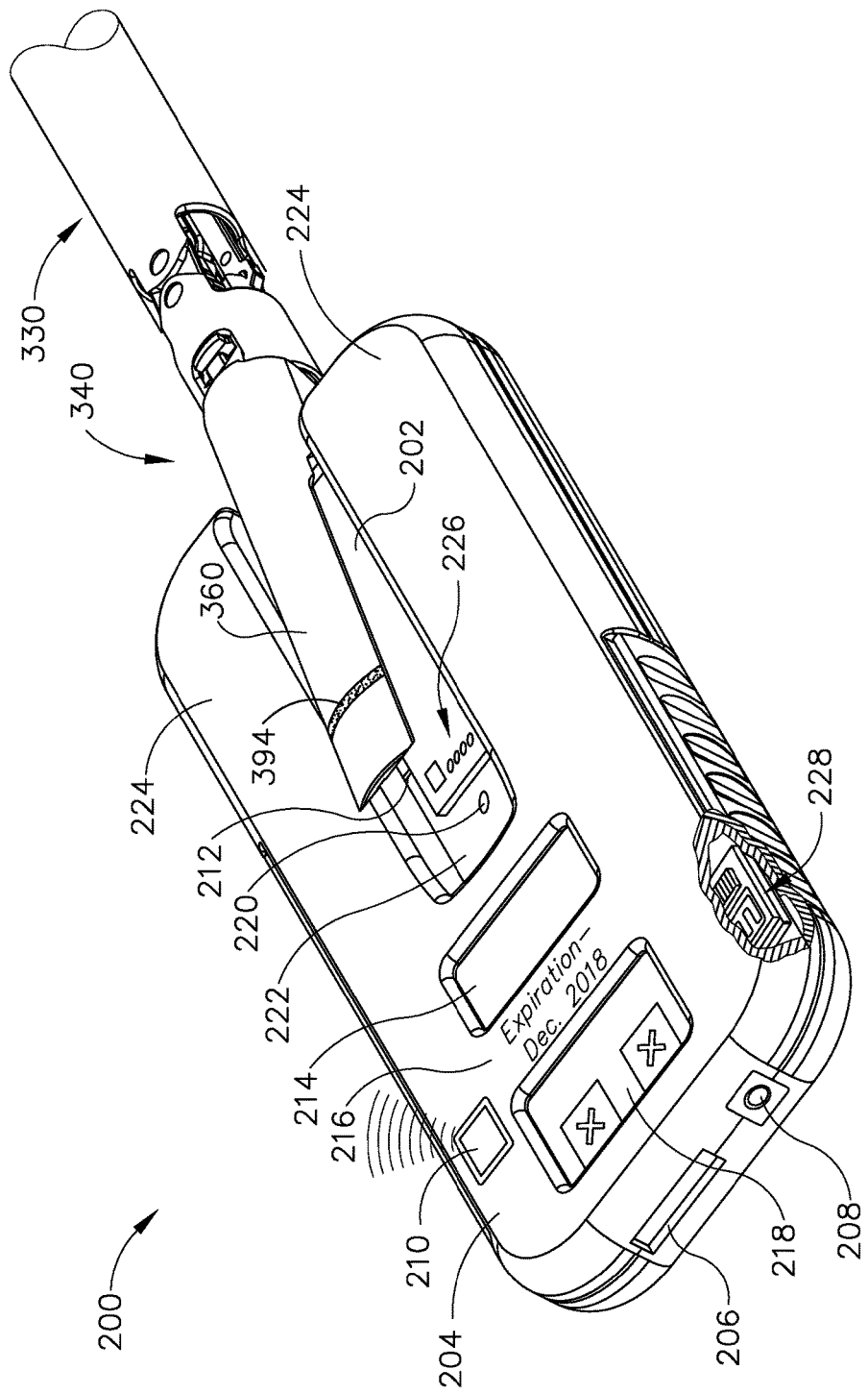
FIG. 11 depicts a perspective view of the end effector of FIG. 9 positioned to engage buttress assemblies of the buttress applier cartridge of FIG. 7.

In the present example, buttress (202) has a length that corresponds to the length of underside (365) of anvil (360); and buttress (201) has a length that corresponds to the length of deck (373) of staple cartridge (370). It may therefore be desirable to ensure that the operator has located end effector (340) at the appropriate longitudinal position in relation to platform (222) when end effector (340) is closed upon buttresses (201, 202), to thereby ensure that buttresses (201, 202) appropriately span the full lengths of deck (373) and underside (365). To that end, platform (222) of the present example further comprises an alignment marking (212). Marking (212) extends perpendicularly relative to the longitudinal axis of platform (222). Marking (212) is configured to correspond with marking (294) of anvil (360), as shown in FIG. 11. Marking (294) of anvil (360) extends perpendicularly relative to the longitudinal axis of anvil (360). Markings (212, 294) are positioned such that markings (212, 294) will align with each other when the operator has located end effector (340) at the appropriate longitudinal position in relation to platform (222). In the event that markings (212, 294) are initially mis-aligned, the operator may simply move end effector (340) and/or cartridge (200) until markings (212, 294) are aligned. The operator may then fully close end effector (340) to pick up buttresses (201, 202) from platform (222).

Figure 13C:
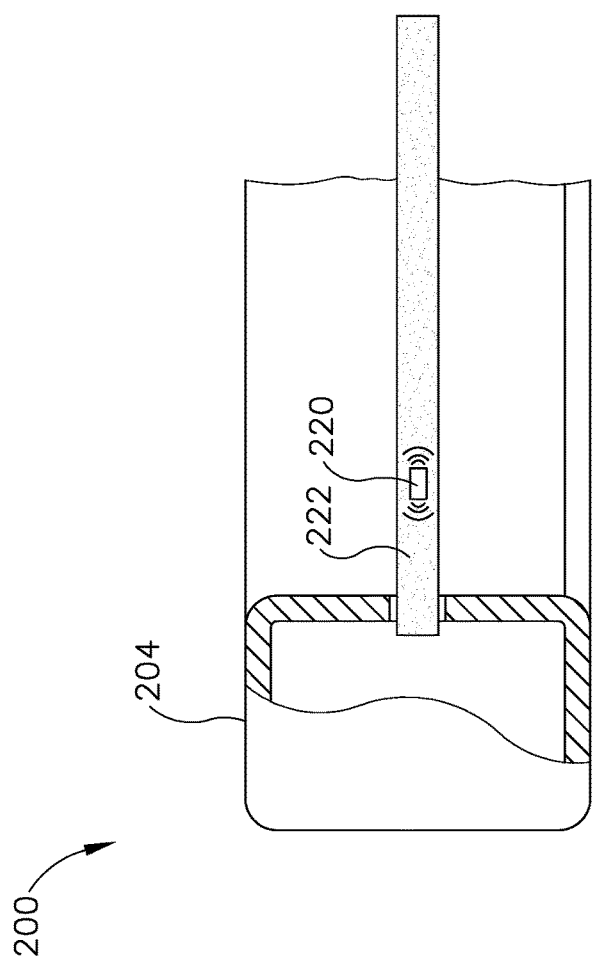
FIG. 13C depicts a cross-sectional side view of the buttress applier cartridge of FIG. 7, with the upper and lower buttress assemblies having been removed by the end effector of FIG. 9.

As best seen in FIGS. 13A-13C, platform (222) of the present example also includes an internal magnet (220). While magnet (220) is in platform (222) in the present example, it should be understood that magnet (220) may alternatively be located in other locations (e.g., in one or both of prongs (224)). Magnet (220) is configured to interact with hall effect sensors (394, 396), which are integrated into staple cartridge (370) and anvil (340). In particular, as shown in FIG. 13B, hall effect sensors (394, 396) sense the magnetic field of magnet (220) when end effector (340) is closed upon buttresses (201, 202) and platform (222). A control circuit that is in communication with sensors (394, 396) may be tuned to determine when the signal from sensors (394, 396) indicates that end effector (340) has closed upon buttresses (201, 202) and platform (222) with a sufficient force. Of course, there are other ways in which such a determination may be made. For instance, a position sensor in end effector (340) may sense the closure angle of anvil (360) relative to staple cartridge (370) and/or a force sensor in end effector (340) may sense the closure pressure being applied by anvil (360) and/or cartridge (370). As another merely illustrative example, platform (222) may include a strain gauge or force sensor, etc. Other suitable components and techniques that may be used to sense whether end effector (340) has closed upon buttresses (201, 202) and platform (222) with a sufficient force will be apparent to those of ordinary skill in the art in view of the teachings herein.

Regardless of the features that are used to determine whether end effector (340) has closed upon buttresses (201, 202) and platform (222) with a sufficient force, the associated data may be used in numerous ways. For instance, in versions where status indicator window (214) is dynamic, status indicator window (214) may be used to provide a visual indication to the operator to indicate that end effector (340) has closed upon buttresses (201, 202) and platform (222) with a sufficient force. As another merely illustrative example, cartridge (200) may include a feature that is operable to emit an audible tone to indicate to the operator to indicate that end effector (340) has closed upon buttresses (201, 202) and platform (222) with a sufficient force. Similar audio and/or visual feedback may be provided through handle assembly (310), in addition to or in lieu of being provided through cartridge (200). For instance, display screen (320) may be used to provide a visual indication to the operator to indicate that end effector (340) has closed upon buttresses (201, 202) and platform (222) with a sufficient force.

Figure 12:
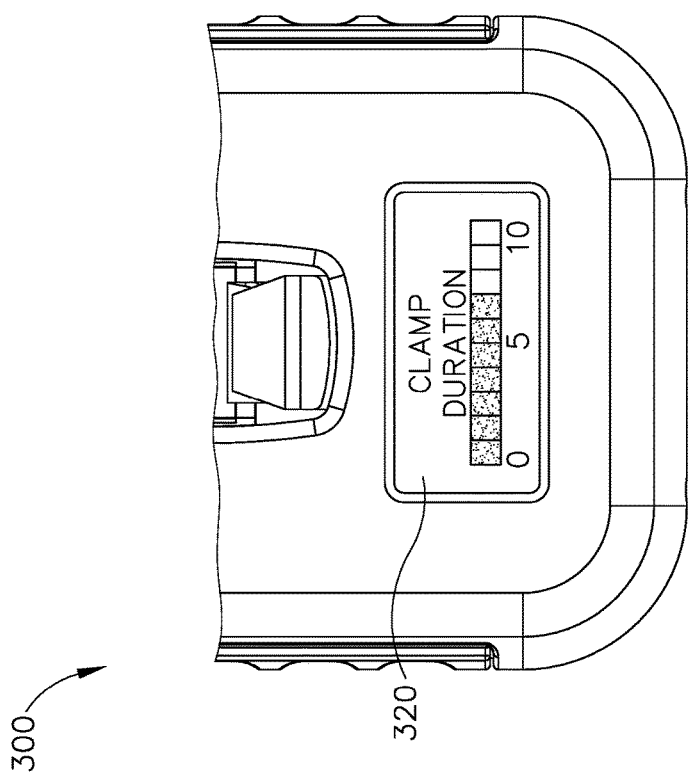
FIG. 12 depicts a top plan view of a display of the handle assembly of FIG. 8.

In some versions, it may be desirable to provide clamping of end effector (340) on buttresses (201, 202) for at least a certain duration in order to ensure proper adhesion of buttresses (201, 202) to end effector (340). To that end, once one or more features detect that end effector (340) has closed upon buttresses (201, 202) and platform (222) with a sufficient force, a control logic may begin a timer to clock the duration of that force. The control logic may then trigger an audible feedback feature and/or visual feedback feature once the sufficient force has been applied for the predetermined duration. In some such versions, a visual feedback feature may provide the operator with a real time count-up or count-down, enabling the operator to view how much more time the operator will need to hold end effector (340) in a closed state. FIG. 12 shows one merely illustrative example of how this may be done through display screen (320). In this example, the control logic begins illuminating discrete visual elements in a linear array when the sufficient force is detected; and further illuminates the visual elements in a progression along the array during the span of the predetermined duration. When all of the visual elements in the array are illuminated, this provides visual feedback to the operator indicating that the predetermined duration has passed. The operator may then open end effector (340) and pull end effector (340) away from cartridge (200). Again, the full illumination of the last visual element in the array may also be accompanied by an audible tone and/or some other form of feedback. Other suitable ways in which an operator may receive feedback indicating whether end effector (340) has sufficiently clamped on buttresses (201, 202) will be apparent to those of ordinary skill in the art in view of the teachings herein.

It should also be understood that different kinds of buttresses (201, 202) may warrant different closure forces from end effector (340) and/or different closure durations in order to be adequately secured to end effector (340). In such instances, a control logic (e.g., in handle assembly (310)) may determine which closure force and/or duration to sense based on the kind of buttress (201, 202) identified by sensors (390, 392) from indicia (226).

Display screen (320) may provide various kinds of information in addition to or in lieu of the information noted above. For instance, display screen (320) may indicate whether buttresses (201, 202) are properly aligned in relation to end effector (340), the initiation of a start-up routine in handle assembly (310), the identity/type of buttresses (201, 202), the kind(s) of medical procedure that the particular buttresses (201, 202) are best suited for, the successful loading of buttresses (201, 202) on end effector (340), warnings and precautions associated with the particular kind of buttresses (201, 202), the thickness of buttresses (201, 202), the thickness of tissue captured between anvil (360) and staple cartridge (370), the presence/type of medicament on buttresses (201, 202), the compression time required for buttresses (201, 202) to be properly adhered to end effector (340), and/or the duration for which the operator may expect buttresses (201, 202) to remain properly adhered to end effector (340). Other kinds of information that may be indicated through display screen (320) will be apparent to those of ordinary skill in the art in view of the teachings herein. It also should be understood that such information may come from various sources, including but not limited to cartridge (200) (e.g., as communicated via transmitter (210)) buttress (201, 202) (e.g., via indicia (226) and sensors (390, 392)); anvil (360); and/or cartridge (370). Other suitable sources of information that may be indicated through display screen (320) will be apparent to those of ordinary skill in the art in view of the teachings herein.

In an exemplary use, the operator views indicator window (214), expiration date listing (216), and environmental condition indicator (218) to confirm that cartridge (200) is appropriate for the present surgical procedure and is ready for use. The operator then positions end effector positions end effector (340) between prongs (224) of housing (204) as shown in FIG. 11. The operator then closes end effector (340) on buttresses (201, 202) and platform (222) as shown in FIG. 13B. This causes sensors (390, 392) to read indicia (226), resulting in visual feedback through display screen (320) indicating information associated with buttresses (201, 202) as noted above. As the operator clamps down on buttresses (201, 202) and platform (222) with end effector (340), hall effect sensors (394, 396) sense the magnetic field of magnet (220) in platform (222). This results in signals that drive visual feedback through display screen (320) as shown in FIG. 12. Once the operator confirms that end effector (340) has been clamped with sufficient force for a sufficient duration, the operator opens end effector (340). Buttresses (201, 202) will be adhered to underside (365) of anvil (360) and deck (373) of cartridge (370) via adhesive layers of buttresses (201, 202), such that the opened end effector (340) will remove buttresses (201, 202) from platform (222) as shown in FIG. 13C. The operator may then use end effector (340) on tissue in accordance with the teachings above in relation to FIGS. 5A-6. Other suitable ways in which cartridge (200) and instrument (300) may be used will be apparent to those of ordinary skill in the art in view of the teachings herein.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising a buttress applier cartridge, wherein the cartridge comprises: (i) a housing defining a gap configured to receive a portion of an end effector of a surgical stapler, (ii) a platform, wherein a portion of the platform is exposed in the gap defined by the housing, (iii) a first buttress assembly positioned on the platform, wherein the first buttress assembly is exposed in the gap defined by the housing, and (iv) a data communication feature, wherein the data communication feature is configured to provide communication of data relating to the cartridge.

Example 2

The apparatus of Example 1, wherein the data communication feature comprises a display, wherein the display is operable to visually render information based on data relating to the cartridge.

Example 3

The apparatus of Example 2, wherein the display is operable to visually indicate a buttress assembly type associated with the first buttress assembly.

Example 4

The apparatus of any one or more of Examples 2 through 3, wherein the display is operable to change the visual rendering based on a change in state of the cartridge.

Example 5

The apparatus of any one or more of Examples 1 through 4, wherein the data communication feature comprises an environmental condition indicator, wherein the environmental condition indicator is configured to render information indicative of an environmental condition to which the cartridge has been exposed.

Example 6

The apparatus of Example 5, wherein the environmental condition indicator is configured to indicate when the cartridge has been exposed to a temperature above a predetermined threshold.

Example 7

The apparatus of any one or more of Examples 5 through 6, wherein the environmental condition indicator is configured to indicate when the cartridge has been exposed to a humidity level above a predetermined threshold.

Example 8

The apparatus of any one or more of Examples 1 through 7, wherein the data communication feature comprises a data port configured to couple with an external device via a wire.

Example 9

The apparatus of any one or more of Examples 1 through 8, wherein the data communication feature comprises a wireless transmitter.

Example 10

The apparatus of any one or more of Examples 1 through 9, wherein the data communication feature comprises a magnet.

Example 11

The apparatus of Example 10, wherein the magnet is located in the platform.

Example 12

The apparatus of any one or more of Examples 1 through 11, further comprising a stapling instrument, wherein the stapling instrument comprises: (i) a shaft assembly, and (ii) an end effector located at a distal end of the shaft assembly, wherein the end effector comprises: (A) an anvil, and (B) a staple cartridge, wherein the anvil is configured to move toward the staple cartridge, wherein the staple cartridge is configured to drive staples toward the anvil.

Example 13

The apparatus of Example 12, wherein the stapling instrument further comprises a data communication feature, wherein the data communication feature of the stapling instrument is further configured to provide communication of data relating to the cartridge.

Example 14

The apparatus of Example 13, wherein the data communication feature of the stapling instrument is configured to cooperate with the data communication feature of the cartridge to thereby provide communication of data relating to the cartridge.

Example 15

The apparatus of Example 14, wherein the data communication feature of the stapling instrument is located in the end effector, wherein the data communication feature of the cartridge is located in the first buttress assembly.

Example 16

The apparatus of any one or more of Examples 1 through 15, further comprising a second buttress assembly.

Example 17

The apparatus of Example 16, wherein the first buttress assembly is located on a first side of the platform, wherein the second buttress assembly is located on the second side of the platform.

Example 18

An apparatus, comprising: (a) a buttress applier cartridge, wherein the cartridge comprises: (i) a housing defining a gap configured to receive a portion of an end effector of a surgical stapler, (ii) a platform, wherein a portion of the platform is exposed in the gap defined by the housing, and (iii) a buttress assembly positioned on the platform, wherein the buttress assembly is exposed in the gap defined by the housing; and (b) a stapling instrument, wherein the stapling instrument comprises: (i) a shaft assembly, (ii) an end effector located at a distal end of the shaft assembly, wherein the end effector comprises: (A) an anvil, and (B) a staple cartridge, wherein the anvil is configured to move toward the staple cartridge, wherein the staple cartridge is configured to drive staples toward the anvil, (iii) a display, wherein the display is configured to render information associated with the cartridge based on one or both of: (A) data communicated form the cartridge to the stapling instrument, or (B) data sensed by one or more sensors in the stapling instrument.

Example 19

A method of operating a stapling instrument, wherein the method comprises: (a) positioning an open end effector of the stapling instrument about a platform of a buttress applier cartridge, wherein the buttress applier cartridge carries at least one buttress assembly; (b) receiving data associated with the cartridge, wherein the data is received through the stapling instrument; and (c) closing the end effector to secure the at least one buttress assembly to the end effector.

Example 20

The method of Example 19, wherein the data is received in response to the act of closing the end effector.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and U.S. patent application Ser. No. 14/871,131, entitled "Method for Applying an Implantable Layer to a Fastener Cartridge," field Sep. 30, 2015, published as U.S. Pub. No. 2017/0086842 on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," field Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System," published Jan. 10, 2013, issued as U.S. Pat. No. 8,884,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising a buttress applier cartridge, wherein the cartridge comprises:
   (i) a housing defining a gap configured to receive a portion of an end effector of a surgical stapler,
   (ii) a platform, wherein a portion of the platform is exposed in the gap defined by the housing,
   (iii) a first buttress assembly positioned on the platform, wherein the first buttress assembly is exposed in the gap defined by the housing, and
   (iv) a data communication feature, wherein the data communication feature is configured to provide communication of data relating to the cartridge;
   wherein the data communication feature comprises an environmental condition indicator, wherein the environmental condition indicator is configured to render information indicative of an environmental condition to which the cartridge has been exposed.

2. The apparatus of claim 1, wherein the data communication feature comprises a display, wherein the display is operable to visually render information based on data relating to the cartridge.

3. The apparatus of claim 2, wherein the display is operable to visually indicate a buttress assembly type associated with the first buttress assembly.

4. The apparatus of claim 2, wherein the display is operable to change the visual rendering based on a change in state of the cartridge.

5. The apparatus of claim 1, wherein the environmental condition indicator is configured to indicate when the cartridge has been exposed to a temperature above a predetermined threshold.

6. The apparatus of claim 1, wherein the environmental condition indicator is configured to indicate when the cartridge has been exposed to a humidity level above a predetermined threshold.

7. The apparatus of claim 1, wherein the data communication feature comprises a data port configured to couple with an external device via a wire.

8. The apparatus of claim 1, wherein the data communication feature comprises a wireless transmitter.

9. The apparatus of claim 1, wherein the data communication feature comprises a magnet.

10. The apparatus of claim 9, wherein the magnet is located in the platform.

11. The apparatus of claim 1, further comprising a stapling instrument, wherein the stapling instrument comprises:
    (i) a shaft assembly, and
    (ii) an end effector located at a distal end of the shaft assembly, wherein the end effector comprises:
      (A) an anvil, and
      (B) a staple cartridge, wherein the anvil is configured to move toward the staple cartridge, wherein the staple cartridge is configured to drive staples toward the anvil.

12. The apparatus of claim 11, wherein the stapling instrument further comprises a data communication feature, wherein the data communication feature of the stapling instrument is further configured to provide communication of data relating to the cartridge.

13. The apparatus of claim 12, wherein the data communication feature of the stapling instrument is configured to cooperate with the data communication feature of the cartridge to thereby provide communication of data relating to the cartridge.

14. The apparatus of claim 13, wherein the data communication feature of the stapling instrument is located in the end effector, wherein at least a portion of the data communication feature of the cartridge is located in the first buttress assembly.

15. The apparatus of claim 1, further comprising a second buttress assembly.

16. The apparatus of claim 15, wherein the first buttress assembly is located on a first side of the platform, wherein the second buttress assembly is located on the second side of the platform.

17. An apparatus, comprising:
   (a) a buttress applier cartridge, wherein the cartridge comprises:
     (i) a housing defining a gap configured to receive a portion of an end effector of a surgical stapler,
     (ii) a platform, wherein a portion of the platform is exposed in the gap defined by the housing,
     (iii) a buttress assembly positioned on the platform, wherein the buttress assembly is exposed in the gap defined by the housing, and
     (iv) a clamp indicator, wherein the clamp indicator is configured to receive a signal indicating an amount of force applied to the buttress assembly and, where the amount of force meets a sufficient force threshold, produce an indication that the amount of force is sufficient; and (b) a stapling instrument, wherein the stapling instrument comprises:
  (i) a shaft assembly,
  (ii) an end effector located at a distal end of the shaft assembly, wherein the end effector comprises:
    (A) an anvil, and
    (B) a staple cartridge, wherein the anvil is configured to move toward the staple cartridge, wherein the staple cartridge is configured to drive staples toward the anvil, and
  (iii) a display, wherein the display is configured to render information associated with the cartridge based on one or both of:
    (A) data communicated form the cartridge to the stapling instrument, or
    (B) data sensed by one or more sensors in the stapling instrument.

18. A method of operating a stapling instrument, wherein the method comprises:
  (a) positioning an open end effector of the stapling instrument about a platform of a buttress applier cartridge, wherein the buttress applier cartridge carries at least one buttress assembly;
  (b) receiving data associated with the cartridge, wherein the data is received through the stapling instrument;
  (c) closing the end effector to secure the at least one buttress assembly to the end effector;
  (d) receiving data indicating an amount of force applied to the at least one buttress assembly;
  (e) tracking an elapsed time during which the end effector is closed; and
  (f) where both the amount of force meets a sufficient force threshold and the elapsed time meets a time threshold, producing an indication that the end effector is secured.

19. The method of claim 18, wherein the indication that the end effector is secured is produced from the buttress applier cartridge.

* * * * *